United States Patent [19]
Bushman

[11] Patent Number: 6,010,860
[45] Date of Patent: Jan. 4, 2000

[54] METHOD FOR SITE-SPECIFIC INTEGRATION OF NUCLEIC ACIDS AND RELATED PRODUCTS

[75] Inventor: Frederic D. Bushman, Encinitas, Calif.

[73] Assignee: The Salk Institute for Biological Studies, La Jolla, Calif.

[21] Appl. No.: 09/203,796

[22] Filed: Dec. 1, 1998

Related U.S. Application Data

[62] Division of application No. 09/062,375, Apr. 17, 1998, which is a division of application No. 08/464,257, Jun. 5, 1995, Pat. No. 5,830,707, which is a division of application No. 08/248,074, May 23, 1994, abandoned.

[51] Int. Cl.$^7$ .......................... C07K 14/05; C07K 14/15; C07K 14/155; C07K 14/16; C12N 9/12; C12N 15/87; C12Q 1/68; C12Q 1/02

[52] U.S. Cl. ................................. 435/6; 435/29; 435/194; 435/455; 435/456; 435/463; 435/468; 435/471; 530/300; 530/350

[58] Field of Search ...................................... 530/300, 350; 435/6, 29, 194, 455, 456, 463, 468, 471

[56] References Cited

U.S. PATENT DOCUMENTS

| | | | |
|---|---|---|---|
| 4,405,712 | 9/1983 | Vande Woude et al. | 435/5 |
| 4,650,764 | 3/1987 | Temin et al. | 435/350 |
| 5,252,479 | 10/1993 | Srivastava | 435/235.1 |

OTHER PUBLICATIONS

Bushman and Craigie, "Activities of human immunodeficiency virus (HIV) integration protein in vitro: Specific cleavage and integration of HIV DNA" *Proc. Natl. Acad. Sci. USA* 88:1339–1343 (1991).

Bushman and Craigie, "Integration of human immunodeficiency virus DNA: Adduct interference analysis of required DNA sites" *Proc. Natl. Acad. Sci. USA* 89:3458–3462 (1992).

Bushman et al., "Domains of the integrase protein of human immunodeficiency virus type 1 responsible for polynucleotidyl transfer and zinc binding" *Proc. Natl. Acad. Sci. USA* 90:3428–3432 (1993).

Clavel et al., "Genetic Recombintion of Human Immunodeficiency Virus" *J. of Virology* 63(3):1455–1459 (1989).

Craigie et al., "The IN Protein of Moloney Murine Leukemia Virus Processes the Viral DNA Ends and Accomplishes Their Integration In Vitro" *Cell* 62:829–837 (1990).

Engelman et al., "HIV–1 DNA Integration: Mechanism of Viral DNA Cleavage and DNA Strand Transfer" *Cell* 67:1211–1221 (1991).

Engelman and Craigie, "Identification of Conserved Amino Acid Residues Critical for Human Immunodeficiency Virus Type 1 Integrase Function In Vitro" *J. of Virology* 66(11):6361–6369 (1992).

Engelman et al., "Identification of discrete functional domains of HIV–1 integrase and their organization within an active multimeric complex" *EMBO Journal* 12(8):3269–3275 (1993).

Goff, Stephen P., "Genetics of Retroviral Integration" *Annu. Rev. Genet.* 26:527–544 (1992).

Johnson et al., "Computer analysis of retroviral pol genes: Assignment of enzymatic functions to specific sequences and homologies with nonviral enzymes" *Proc. Natl. Acad. Sci. USA* 83:7648–7652 (1986).

King et al., "Glu-111 Is Required for Activation of the DNA Cleavage Center of EcoRI Endonuclease" *J. of Biological Chemistry* 264(20):11807–11815 (1989).

Kulkosky et al., "Residues Critical for Retroviral Integrative Recombination in a Region That Is Highly Conserved among Retroviral/Retrotransposon Integrases and Bacterial Insertion Sequence Transposases" *Molecular and Cellular Biology* 12(5):2331–2338 (1992).

Leavitt et al., "Both Substrate and Target Oligonucleotide Sequences Affect In Vitro Integration Mediated by Human Immunodeficiency Virus Type 1 Integrase Protein Produced in *Saccharomyces cerevisiae*" *J. of Virology* 66(4):2359–2368 (1992).

Morgan, Richard A., "Human Gene Therapy" *BioPharm* 6(1):32–35 (1993).

*Primary Examiner*—Terry McKelvey
*Attorney, Agent, or Firm*—Gray Cary Ware & Freidenrich; Stephen E. Reiter

[57] ABSTRACT

Chimeric proteins are provided comprising a first domain that attaches said chimeric protein to a target nucleic acid, and a second domain that integrates donor nucleic acid into a target nucleic acid. Also provided are nucleic acid constructs, recombinant vectors encoding invention chimeric proteins, recombinant retroviruses, and related methods.

18 Claims, 4 Drawing Sheets

R8

R8 Vif⁻

R8 Vif⁻HAHT

R8 Vif⁻λR-IN

R8 Vif⁻IN-STF

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (ii) MOLECULE TYPE: Oligonucleotide (xi) SEQUENCE DESCRIPTION: SEQ ID NO:1:

ACTGCTAGAG ATTTTCCACA CGGATCCTAG GC      32

(2) INFORMATION FOR SEQ ID NO:2:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (ii) MOLECULE TYPE: Oligonucleotide (xi) SEQUENCE DESCRIPTION: SEQ ID NO:2:

GCCTAGGATC CGTGTGGAAA ATCTCTAGCA TG      32

(2) INFORMATION FOR SEQ ID NO:3:

(i) SEQUENCE CHARACTERISTICS:
      (A) LENGTH: 66 base pairs
      (B) TYPE: nucleic acid
      (C) STRANDEDNESS: both
      (D) TOPOLOGY: linear (ii) MOLECULE TYPE: Oligonucleotide (xi) SEQUENCE DESCRIPTION: SEQ ID NO:3:

ACTGCTAGAG ATTTTCCACA CGGATCCTAG GCTTTTGCCT AGGATCCGTG TGGAAAATCT      60

CTAGCA      66

(2) INFORMATION FOR SEQ ID NO:4:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: Oligonucleotide (xi) SEQUENCE DESCRIPTION: SEQ ID NO:4:

```
GCCTAGGATC CGTGTGGAAA ATC                                                    23

(2) INFORMATION FOR SEQ ID NO:5:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: Oligonucleotide (xi) SEQUENCE DESCRIPTION: SEQ ID NO:5:

GACAGATTCC TGGGATAAGC CAAG                                                   24

(2) INFORMATION FOR SEQ ID NO:6:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: Oligonucleotide (xi) SEQUENCE DESCRIPTION: SEQ ID NO:6:

CGCGCTTTGA TATACGCCGA GATC                                                   24

(2) INFORMATION FOR SEQ ID NO:7:

(i) SEQUENCE CHARACTERISTICS:
          (A) LENGTH: 38 base pairs
          (B) TYPE: nucleic acid
          (C) STRANDEDNESS: both
          (D) TOPOLOGY: linear (ii) MOLECULE TYPE: Oligonucleotide (xi) SEQUENCE DESCRIPTION: SEQ ID NO:7:

GCCGAAGCAT CGATGCAGCA GAACCGGAGG AGAATAAG                                    38

(2) INFORMATION FOR SEQ ID NO:8:

(i) SEQUENCE CHARACTERISTICS:
          (A) LENGTH: 41 base pairs
          (B) TYPE: nucleic acid
          (C) STRANDEDNESS: both
          (D) TOPOLOGY: linear (ii) MOLECULE TYPE: Oligonucleotide (xi) SEQUENCE DESCRIPTION: SEQ ID NO:8:

TTTGCATCAT CGCCCTGTTG CTCGACTGGG CCCTACGTGG C                                41

(2) INFORMATION FOR SEQ ID NO:9:

(i) SEQUENCE CHARACTERISTICS:
          (A) LENGTH: 60 base pairs
          (B) TYPE: nucleic acid
          (C) STRANDEDNESS: both
          (D) TOPOLOGY: linear (ii) MOLECULE TYPE: Oligonucleotide (xi) SEQUENCE DESCRIPTION: SEQ ID NO:9:

AGTGCTGGAA TCAGGAAAGT ACTAAACTTT CCGCAGATGA GCACAAAAAA GAAACCATTA            60

(2) INFORMATION FOR SEQ ID NO:10:
```

```
       (i) SEQUENCE CHARACTERISTICS:
           (A) LENGTH: 39 base pairs
           (B) TYPE: nucleic acid
           (C) STRANDEDNESS: both
           (D) TOPOLOGY: linear (ii) MOLECULE TYPE: cDNA (xi) SEQUENCE DESCRIPTION: SEQ ID NO:10:

GCGGAGAGAT GGGTGTCGAC ACATATGTTT TTAGATGGA                                39
```

METHOD FOR SITE-SPECIFIC INTEGRATION OF NUCLEIC ACIDS AND RELATED PRODUCTS

This application is a divisional of application Ser. No. 09/062,375, filed on Apr. 17, 1998, now pending, which is a divisional of application Ser. No. 08/464,257, filed on Jun. 5, 1995, now issued as U.S. Pat. No. 5,830,707, which is a divisional of application Ser. No. 08/248,074, filed May 23, 1994, now abandoned; the entire contents of each of which are hereby incorporated by reference herein.

ACKNOWLEDGEMENT

This invention was made with Government support under Grant Number R01-AI 34786-0104, awarded by the National Institutes of Health. The Government has certain rights in this invention.

BACKGROUND OF THE INVENTION

The role of DNA integration in the HIV-1 life cycle has been well characterized. Following binding of HIV-1 to a sensitive cell, the viral and cellular membranes fuse and the viral core particle is released into the cytoplasm. There the viral genomic RNA is reverse transcribed, yielding a double stranded DNA copy of the viral RNA genome. Next, a complex of viral DNA and proteins—the "preintegration complex"—covalently attaches the viral cDNA to host DNA. The integration step is required for replication, as demonstrated for example by the finding that HIV derivatives containing lesions in the integrase protein are unable to replicate (Clavel et al., (1989) *J. Virol.* 63:1455–1459 and Shin et al., (1994) *J. Virol.* 68:1633–1642). Integration completes the formation of a provirus, which contains all the information necessary to direct the synthesis of the viral RNAs and proteins required for the formation of new virions (Goff, S. P. (1992) *Annu. Rev. Genet.* 26:527–544).

In vivo, integration of retroviral DNA specifically requires the viral-encoded integrase protein (Clavel, F. et al., (1989), *J. Virol.* 63:1455–1459), and DNA sites at each end of the unintegrated viral DNA (Colicelli, J. et al. (1985) *Cell* 42:573–580 and Panganiban, A. T. et al. (1983) *Nature* 306:155–160). Integrase protein is normally synthesized as a part of the gag-pol precursor, and is released from the carboxy-terminus of reverse transcriptase by the action of the viral protease.

Purified integrase protein is capable of catalyzing the formation of a covalent bond between a model viral DNA and a target DNA in vitro (Bushman, F. D. et al. (1991) *Proc. Natl. Acad. Sci. USA* 88:1339–1343, Bushman, F. D. et al. (1990) *Science* 249:1555–1558 and Craigie, R. et al. (1990) *Cell* 62:829–837). Data presented in the references establishes that integrase is not just a required cofactor, but instead is the true recombinase that joins viral DNA to host DNA.

In vivo, prior to integration, the blunt ended DNA product of reverse transcription is cleaved so as to remove two nucleotides from each 3' end. The recessed 3' ends are then joined to 5' ends of breaks made in the target DNA. The resulting integration intermediate is then processed, probably by host DNA repair enzymes, to complete the attachment of each viral 5' end to host DNA (FIG. 1a) (for a recent review see Goff, S. P. (1992) *Annu. Rev. Genet.* 26:527–544).

In reactions in vitro, purified integrase can cleave the 3' end of a model viral end-substrate and catalyze covalent integration of the recessed 3' end into a target DNA (FIG. 1b) (Bushman, F. D. et al. (1990) *Science* 249:1555–1558, Craigie, R. et al. (1990) *Cell* 62:829–837 and Katz, R. A. et al. (1990) *Cell* 63:87–95). The product of these reactions resembles the unrepaired intermediate generated during integration in vivo. There is little specificity, however, both in vivo and in vitro in the target DNA sequence in which integration occurs.

Despite safety concerns, retroviral vectors are currently a popular means for delivering DNA in gene therapy protocols. Attractive features include controllable cell type specificity of delivery, stable insertion of the delivered genes into the host genome, and stable maintenance of genes once integrated. Genes can either be delivered in replication competent viruses (i.e., a heterologous coding region in a viral genome) or, more commonly, as retroviral vectors. In retroviral vector systems, packaging cell lines are used that express the viral proteins from unpackagable RNAs. A DNA construct containing the gene of interest flanked by LTRs and a packaging signal sequence ($\psi$) is introduced in the packaging cell line (see, e.g., Rosenberg, S. A., 1990, *New Enql. J. Med.*, 323:570–578). Because the only packagable RNA is encoded by the vector sequences, the viral particles produced contain exclusively the therapeutic gene. Infection of a target cell then results in reverse transcription and integration of the therapeutic gene. As a result of these attractive features, many of the protocols so far approved for human gene therapy employ retroviral delivery systems (Morgan, R., 1993, *BioPharm*, 6(1):32–35).

Many studies in vertebrate systems establish that insertion of retroviral DNA can result in inactivation or ectopic activation of cellular genes, thereby causing diseases (for a recent review see Lee, Y. M. H., et al. (1990) *J. Virol.* 64:5958–5965). This represents a serious safety concern in using retroviral gene delivery systems in human systems. One well studied consequence of retroviral integration is activation of oncogenes. Several probable cases of activation of a human oncogene by insertion of HIV have been described (Shiramizu et al., 1994, *Cancer Res.*, 54:2069–2072). Thus, methods for site-specifically controlling the location of integration of retroviral vectors are desired to overcome the prior art problem of insertional mutagenesis of the host genome.

In addition, researchers who identify important DNA-binding proteins by genetic assays also wish to identify the genes regulated by these proteins. Examples include the identification of regulatory genes associated with chromosomal breakpoints in tumors (e.g., Djabali, et al., 1992, *Nature Genetics*, 2:113–118; and Kinzler and Vogelstein, 1990, *Mol. Cel. Biol.*, 10:634–642) and the discovery of regulatory genes associated with developmental defects in humans and other organisms. Thus, new in vitro methods for rapidly locating and isolating the genes controlled by DNA-binding proteins are desired.

BRIEF DESCRIPTION OF THE INVENTION

In accordance with the present invention, there are provided chimeric proteins comprising a first domain that attaches the chimeric protein to a target nucleic acid, and a second domain that integrates donor nucleic acid into the target nucleic acid. Invention proteins are useful for targeting and integrating donor nucleic acids at specific locations on target nucleic acids, and for facilitating the identification (i.e., location and isolation) of desired genes.

Also provided are nucleic acid constructs encoding chimeric proteins of the invention, recombinant vectors comprising such nucleic acids, and host cells containing same.

Invention constructs, vectors and host cells are useful for the recombinant production of the above-described chimeric proteins.

In accordance with another embodiment of the present invention, there are provided recombinant retroviruses for site-specific integration into a target nucleic acid comprising an invention chimeric protein. Recombinant retroviruses of the invention are useful as attenuated viral vaccines or as a vectors for gene therapy methods.

In accordance with a further embodiment of the present invention, there are provided methods for site-specific control of donor nucleic acid integration into target nucleic acid. Such method comprises contacting target nucleic acid with an invention chimeric protein, in the presence of donor nucleic acid.

In accordance with still another embodiment of the present invention, there are provided methods for locating specific gene(s) comprising contacting target nucleic acid containing regulatory regions associated with specific gene(s) with an invention chimeric protein, in the presence of donor nucleic acid, and detecting the site of integration of the donor nucleic acid.

BRIEF DESCRIPTION OF THE FIGURES

FIGS. 1a–1b depict the DNA cutting and joining reactions mediating retroviral integration. Donor nucleic acid is shown as the dark ladder, target nucleic acid is shown as the light ladder, and 5' DNA ends are shown as dark balls. FIG. 1, panel (b) illustrates reactions carried out by purified HIV-1 integrase in vitro.

DETAILED DESCRIPTION OF THE INVENTION

Figure 1:
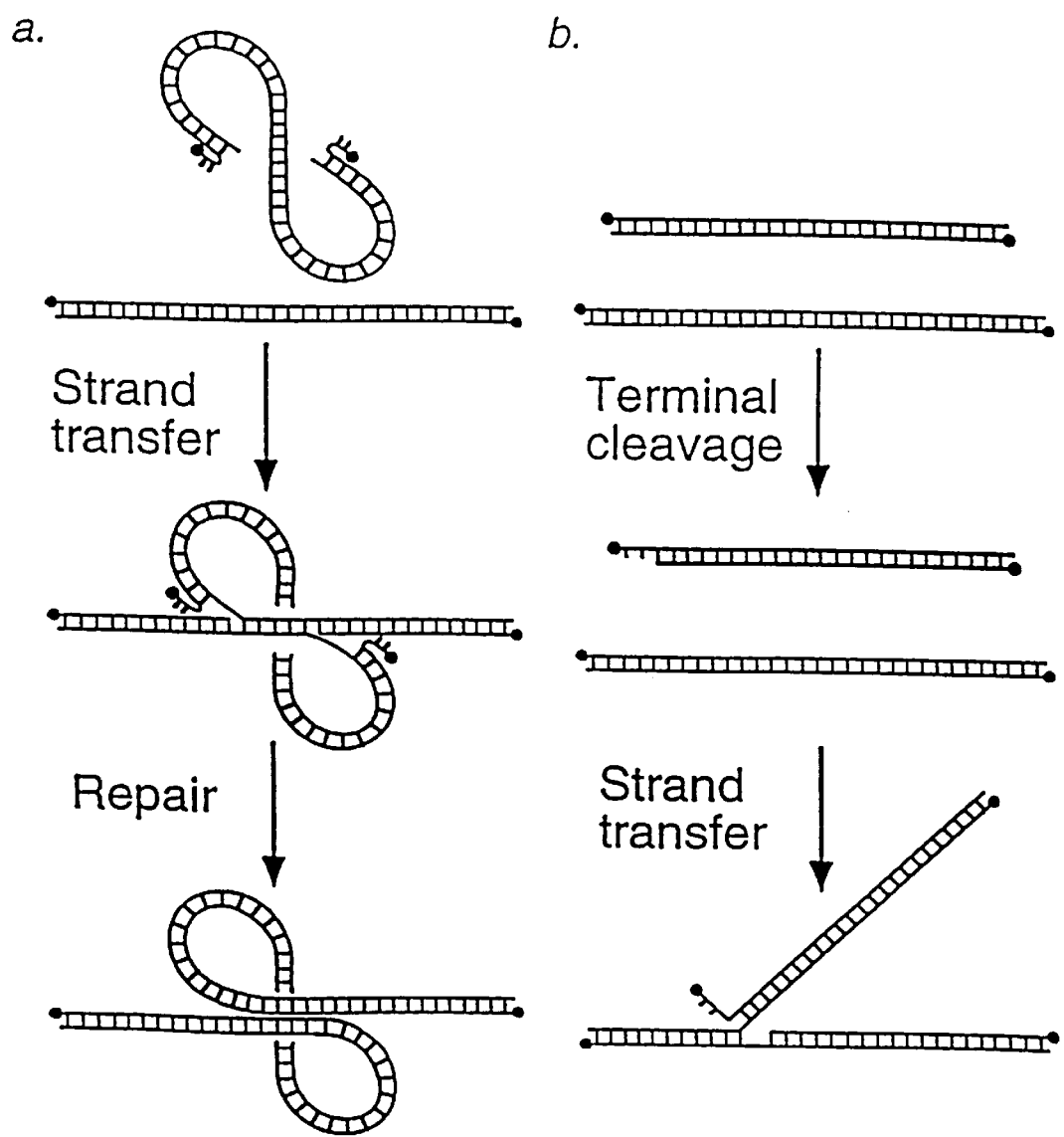
FIG. 1, panel (a) illustrates reactions mediating integration in vivo.

The chimeric proteins of the invention comprise a first domain that attaches the chimeric protein to target nucleic acid, and a second domain that integrates donor nucleic acid into the target nucleic acid. As employed herein, the phrase "chimeric protein" refers to a genetically engineered recombinant protein wherein the domains thereof are derived from heterologous coding regions (i.e., coding regions obtained from different genes).

As used herein, "first domain" refers to the domain within the invention chimeric protein that functions to attach the chimeric protein to a specific recognition sequence on a target nucleic acid. The first domain is at least 5 amino acids in length and can be located anywhere within the chimeric protein, e.g., internally, or at the amino or carboxy termini thereof. The first domain can be either a "DNA-binding domain" or a "protein-binding domain" that is operative to couple and/or associate the chimeric protein with a recognition sequence on the target nucleic acid.

DNA-binding domains are typically derived from DNA-binding proteins. Such DNA-binding domains are known to function heterologously in combination with other functional protein domains by maintaining the ability to bind the natural DNA recognition sequence (see, e.g., Brent and Ptashne, 1985, $Cell$, 43:729–736). For example, hormone receptors are known to have interchangeable DNA-binding domains that function in chimeric proteins (see, e.g., U.S. Pat. No. 4,981,784; and Evans, R., 1988, $Science$, 240:889–895).

As used herein, the term "DNA-binding domain" encompasses a minimal peptide sequence of a DNA-binding protein, up to the entire length of a DNA-binding protein, so long as the DNA-binding domain functions to associate with target nucleic acid. In other words, when a DNA-binding domain is employed in the invention chimeric protein, the association of the invention chimeric protein with the target nucleic acid occurs by direct binding. The DNA-binding domain tethers the second domain (i.e., the integrating domain) in close proximity to a specific recognition sequence on the target nucleic acid so that a desired donor nucleic acid can be integrated into the target nucleic acid sequence.

"DNA-binding protein(s)" utilized herein belong to a well-known class of proteins that are able to directly bind DNA and perform a variety of functions, such as facilitate initiation of transcription or repression of transcription. Exemplary DNA-binding proteins for use herein include transcription control proteins (e.g., transcription factors and the like; Conaway and Conaway, 1994, "Transcription Mechanisms and Regulation", $Raven\ Press\ Series\ on\ Molecular\ and\ Cellular\ Biology$, Vol. 3, Raven Press, Ltd., New York, N.Y.); recombination enzymes (e.g., hin recombinase, and the like); and DNA modifying enzymes (e.g., restriction enzymes, and the like).

Suitable transcription factors for use herein include, e.g., homeobox proteins, zinc finger proteins, hormone receptors, helix-turn-helix proteins, helix-loop-helix proteins, basic-Zip proteins (bZip), β-ribbon factors, and the like. See, for example, Harrison, S., "A Structural Taxonomy of DNA-binding Domains," $Nature$, 353:715–719.

Homeobox DNA-binding proteins suitable for use herein include, for example, HOX, STF-1 (Leonard et al., 1993, $Mol.\ Endo.$, 7:1275–1283), Antp, Mat α-2, INV, and the like. See, also, Scott et al. (1989), $Biochem.\ Biophys.\ Acta$, 989:25–48. It has been found that a fragment of 76 amino acids (corresponding to a.a. 140–215 described in Leonard et al., 1993, $Mol.\ Endo.$, 7:1275–1283) containing the STF-1 homeodomain binds DNA as tightly as wild-type STF-1.

Suitable zinc finger DNA-binding proteins for use herein include, Zif268, GLI, XFin, and the like. See also, Klug and Rhodes (1987), $Trends\ Biochem.\ Sci.$, 12:464; Jacobs and Michaels (1990), $New\ Biol.$, 2:583; and Jacobs (1992), $EMBO\ J.$, 11:4507–4517.

Exemplary hormone receptor DNA-binding proteins for use herein include, glucocorticoid receptor, thyroid hormone receptor, estrogen receptor, and the like (see, e.g., U.S. Pat. Nos. 4,981,784; 5,171,671; and 5,071,773).

Suitable helix-turn-helix DNA-binding proteins for use herein include, λ-repressor, cro-repressor, 434 repressor, 434-cro, and the like (See, e.g., Pabo and Sauer, 1984, $Annu.\ Rev.\ Biochem.$, 53:293–321).

Exemplary helix-loop-helix DNA-binding proteins for use herein include, MRF4 (Block et al., 1992, $Mol.\ and\ Cell\ Biol.$, 12(6):2484–2492), CTF4 (Tsay et al., 1992, $NAR$, 20(10):2624), NSCL, PAL2, USF, and the like. See, for review, Wright (1992), $Current\ Opinion\ in\ Genetics\ and\ Development$, 2(2):243–248; Kadesch, T. (1992), $Immun.\ Today$, 13(1):31–36; and Garell and Campuzano (1991), $Bioessays$, 13(10):493–498.

Exemplary basic Zip DNA-binding proteins for use herein include, GCN4, fos, jun, and the like (see, for review, Lamb and McKnight, 1991, *Trends Biochem. Sci.*, 16:417–422). Exemplary β-ribbon factors for use herein include, Met-J, ARC, and MNT, and the like.

Suitable recombination enzymes for use herein include, for example, the hin family of recombinases (e. g., hin, gin, pin, and cin; see, Feng et al., 1994, *Science*, 263:348–355), the λ-integrase family, flp-recombinase, TN916 transposons, the resolvase family (e.g., TN21 resolvase), and the like.

DNA-modifying enzymes suitable for use herein include, for example, restriction enzymes, DNA-repair enzymes, site-specific methylases, and the like. For use in the instant invention, restriction enzymes are modified using methods well-known in the art to remove the restriction digest function from the protein while maintaining the DNA-binding function (see, e.g., King et al., 1989, *J. Biol. Chem.*, 264 (20):11807–11815). Thus, any restriction enzyme may be employed herein. The utilization of a restriction enzyme recognizing a rare DNA sequence permits attachment of the invention chimeric protein to relatively few sites on a particular stretch of genomic DNA.

The modification of existing DNA-binding domains to recognize new target recognition sequences is also contemplated herein. It has been found that in vitro evolution methods can be applied to modify and improve existing DNA-binding domains (see, e.g., Devlin et al., 1990, *Science*, 249:404–406; and Scott and Smith, 1990, *Science*, 249:386–390).

"Protein -binding domain(s)" suitable for use as the "first domain" of the invention chimeric protein is typically derived from proteins able to bind another protein (e.g., a transcription factor) that is either directly or indirectly attached (coupled) to the target nucleic acid sequence. Thus, when a protein-binding domain is employed as the first domain, the association of the invention chimeric protein with the target nucleic acid occurs by indirect binding. Suitable protein-binding domains may be obtained, for example, from viral transcription factors (e.g., HSV-VP16, adenovirus E1A, and the like), cellular transcription factors, and the like.

In addition to readily available protein-binding domains, small protein-binding domains, e.g., in the range of about 5–25 amino acids, can be obtained employing the "phage display library" methods described above (Rebar and Pabo, 1994, *Science*, 263:671–673). It has been found that short peptides can be isolated using phage display libraries that bind to an arbitrarily chosen protein. For example, a peptide was obtained from a library displaying random amino-acid hexamers on the surface of a phage that bound specifically to avidin; this peptide bore no similarity to any known avidin ligands (Devlin et al., 1990, *Science*, 249:404–406). This well-known method can be used to create protein-binding domains that bind to proteins already bound in vivo to desired target nucleic acid.

As used herein, "second domain" of the invention chimeric protein refers to the domain within the invention chimeric protein that functions to promote integration of donor nucleic acid into target nucleic acid. The second domain can be located anywhere within the chimeric protein, e.g., internally, or at the amino or carboxy termini thereof.

Typically, the second domain of the invention chimeric protein is derived from an integrase protein, or functionally equivalent fragments thereof. Either the integrating domain or the entire integrase protein may be utilized as a second domain. As used herein, "integrase protein" refers to well-known proteins capable of integrating donor nucleic acid into target nucleic acid (see, Engleman and Craigie, 1992, *J. Virol.*, 66(11):6361–6369). Any integrase protein is suitable for use herein so long as it capable of recognizing a specific donor nucleic acid, and facilitating the integration of donor nucleic acids into a target nucleic acid. Suitable integrase proteins can be derived from retroviral integrases, retrotransposon integrases (e.g., yeast Tyl-Ty5; Boeke, J., pp. 335–375, "Transposable Elements in *S. cerevisiae*, in *Mobil DNA*, Berg and Howe, American Society for Microbiology, Washington, D.C., 1989), and the like.

A particularly preferred integrase protein is a retroviral integrase, which is known to facilitate the integration of retroviral genomes into genomes of infected cells. Retroviral integrase proteins are typically encoded as part of the gag-pol precursor of retroviruses. Suitable retroviral integrase proteins for use herein may be derived from retroviruses such as: human immunodeficiency virus-1, strain NL43 (HIV-1) (Adachi et al. (1986), *J. Virol.*, 59:284–281); HIV-2 (Guyader et al. (1987), *Nature*, 326:662–669); human foamy virus (HFV) (Pahl and Flugel, (1993), *J. Virol.*, 67:5426–5434); Feline immunodeficiency virus (FIV) (Vink et al. (1994), *J. Virol.*, 68:1468–1474); HTLV-1 (Seiki et al. (1983) *PNAS*, 80:3618–3622); Moloney murine leukemia virus (Mo-MLV) (Craigie et al. (1990), *Cell*, 62:829–837); bovine leukemia virus (Rice et al. (1985), *Virology*, 142:357–377); Rous sarcoma virus (RSV), (Schwartz et al. (1983), *Cell*, 32:853–869); mouse mammary tumor virus (MMTV) (Moore et al. (1987), *J. Virol.*, 61:480–490); simian immunodeficiency virus (SIV) (Fomsgaard et al. (1991), *Virology*, 182:397–402; and Regier et al., *AIDS Res. and Hum. Retroviruses*, 6:1221–1231); and the like. See, Engleman and Craigie, 1992, *J. Virology*, 66(11):6361–6369, for additional citations to publications describing other retroviral integrase proteins. As described above, once a nucleic acid sequence encoding an integrase protein is ascertained, the production and isolation of the cDNA for use in expression constructs is well within the skill in the art.

The skilled artisan can determine, by well-known methods such as deletion analysis, the minimum peptide sequence or part of the integrase protein that is required to allow function as an integration domain, i.e., stable integration. The skilled artisan can also determine which modifications of the sequence can be tolerated while maintaining the ability of the integration domain to direct stable integration.

Integration of donor nucleic acid into target nucleic acid, as taught herein, refers to the stable incorporation of donor nucleic acid into target nucleic acid such that the donor nucleic acid becomes permanently associated within the target. The present invention enables stable incorporation of a variety of donor nucleic acids into endogenous genomic DNA in a variety of cells, and ensures stable maintenance and replication in the host cell.

As used herein, "donor nucleic acid" refers to either a single- or double-stranded nucleic acid molecule, preferably double-stranded, comprising a sequence that functions as an integration signal. The donor nucleic acid can vary in length so long as it contains at least about 4 nucleotides, preferably at least about 10 nucleotides, with at least about 25 nucleotides up to about 15 kb being especially preferred. The donor nucleic acid can be in the form of a synthetic oligonucleotide, an expression vector, retroviral vector, viral genome (e.g., derived from a recombinant retrovirus), and the like.

In a preferred embodiment of the invention, the donor nucleic acid contains at least one end region of a retroviral LTR, which provides the integration signal. The end regions of retroviral LTRs (e.g., the U5 and U3 regions) have been found to be sufficient for rendering a nucleic acid containing such a sequence able to integrate into a target nucleic acid. See, for example, Colicelli et al. (1985), *Cell*, 42:573–580; and Panganiban and Temin (1983), *Nature*, 306:155–160.

As used herein, "end region of a retroviral LTR" refers to, as a minimum, a single adenine ("A") nucleotide at the 3' end of a donor nucleic acid. Preferably, the end region comprises at least 4, more preferably at least 10, yet more preferably at least 20, nucleotides selected from a U5 or U3 end of a retroviral LTR sequence.

As used herein, the phrase "retroviral LTR" refers to the well-known repeat sequences that occur at the extreme ends of retroviral genomic DNA (See, e.g., U.S. Pat. No. 4,405, 712). For the practice of the present invention, the phrases "retroviral LTR" and "end region of a retroviral LTR" can be used interchangeably. The skilled artisan can determine, by well-known methods such as deletion analysis, the minimum sequence or part of the retroviral LTR that is required to permit integration. The skilled artisan can also determine which modifications of the LTR sequence can be tolerated while maintaining the ability of the terminal repeat to direct stable, site-specific integration.

Site-specific integration can be assessed, for example, by Southern blot analysis, wherein DNA isolated from cells transduced with donor nucleic acid and digested with a variety of restriction enzymes, is analyzed on Southern blots with a retroviral LTR specific probe. A single band of hybridization evidences site-specific integration. Other methods known to the skilled artisan, such as polymerase chain reaction (PCR) analysis of chromosomal DNA, can also be used to assess stable integration. Alternatively, genomic DNA libraries can be produced from virus infected cells, and genomic clones containing viral DNA can be isolated using HIV sequences as probes. The host DNA used as the DNA integration site can then be sequenced using conventional methodology. Each of these methods allows the exact sequence of the integration site to be determined.

As used herein, "target nucleic acid" refers to any single or double stranded nucleic acid, preferably double stranded, into which integration of donor nucleic acid is desired. Exemplary target nucleic acids include, e.g., genomic DNA (i.e., intact and/or fragmented chromosomal DNA), cDNA, and the like. The target nucleic acid contains at least one binding domain "recognition sequence" which directly or indirectly attaches (binds to) the first domain of the invention chimeric protein. The recognition sequence may be present in more than one location in a target nucleic acid.

The particular sequence recognized on the target nucleic acid depends on the first domain incorporated in the invention chimeric protein. The versatility of the invention resides in part in the ability to select binding domains that bind directly or indirectly to desired recognition sequences on the target nucleic acid. For example, exemplary recognition sequences in target nucleic acid contemplated for attaching an invention chimeric protein include: tissue specific promoters, long interspersed nuclear elements (LINEs, e.g., L1 retrotransposon), short interspersed nuclear elements (SINEs, e.g., Alu repeats), and the like. Also ontemplated are recognition sequences for rare-cutting estriction enzymes (e.g., Srf 1, and the like).

In accordance with another embodiment of the present invention, there are provided nucleic acid constructs encoding chimeric proteins according to the present invention. These constructs are useful for the recombinant expression of the invention chimeric proteins.

Nucleic acid constructs of the invention can be assembled utilizing numerous genomic and cDNA nucleic acid sequences well-known in the art that encode a variety of DNA-binding proteins and integrase proteins. Typically, nucleic acid sequence information for a desired protein can be located in one of many public access databases, e.g., GENBANK, EMBL, Swiss-Prot, and PIR, or in many of the biology related journal publications. Thus, one of skill in the art has access to nucleic acid information for virtually all known genes whose sequence has been published. One of skill in the art can either obtain the corresponding nucleic acid molecule directly from a public depository, or the institution that published the sequence. Optionally, once the nucleic acid sequence encoding a desired protein has been ascertained, the skilled artisan can employ routine methods (e.g., chemical synthesis, or polymerase chain reaction (PCR) amplification) to obtain the desired nucleic acid molecule. The CDNA encoding the desired protein can then be used to make nucleic acid expression constructs and vectors as described herein (see, e.g., Vallette, et al., 1989, *NAR*, 17:723–733; and Yon and Fried, 1989, *NAR*, 17:4895). Thus, virtually all known nucleic acids encoding DNA-binding proteins (and integrase proteins) of interest are available for use in the methods and products described herein.

Nucleic acid constructs encoding invention chimeric proteins may be directly used for expressing the protein in cell free expression systems well-known in the art, or may be incorporated into suitable expression vectors to express and produce the chimeric protein in suitable host cells.

As used herein, the term "expression vector" refers to a recombinant nucleic acid molecule that is used to transport heterologous nucleic acid into cells for expression and/or replication thereof. The expression vector may be either circular or linear, and is capable of incorporating a variety of nucleic acid constructs therein. Expression vectors typically come in the form of a plasmid that, upon introduction into an appropriate host cell, results in expression of the inserted DNA. Expression vectors suitable for use in the practice of the present invention are well known to those of skill in the art and include those that are replicable in eukaryotic cells and/or prokaryotic cells as well as those that remain episomal and those that integrate into the host cell genome. Expression vectors typically further contain other functionally important nucleic acid sequences, such as expression cassettes encoding antibiotic resistance proteins, and the like.

Exemplary expression vectors for transformation of *E. coli* prokaryotic cells include the pET expression vectors (Novagen, Madison, Wis., see U.S. Pat. No. 4,952,496), e.g., pETlla, which contains the T7 promoter, T7 terminator, the inducible *E. coli* lac operator, and the lac repressor gene; and pET 12a-c, which contains the T7 promoter, T7 terminator, and the *E. coli* ompT secretion signal. Another such vector is the pIN-IIIompA2 (see Duffaud et al., *Meth. in Enzymology*, 153:492–507, 1987), which contains the lpp promoter, the lacUV5 promoter operator, the ompA secretion signal, and the lac repressor gene.

Exemplary eukaryotic expression vectors include eukaryotic cassettes, such as the pSV-2 gpt system (Mulligan et al., 1979, *Nature*, 277:108–114); the Okayama-Berg system (*Mol. Cell Biol.*, 2:161–170), and the expression cloning vector described by Genetics Institute (1985, *Science*, 228:810–815). Each of these plasmid vectors are capable of promoting expression of the invention chimeric protein of interest.

Suitable means for introducing (transducing) expression vectors containing invention nucleic acid constructs into host cells to produce transduced recombinant cells (i.e., cells containing recombinant heterologous nucleic acid) are well-known in the art (see, for review, Friedmann, 1989, *Science*, 244:1275–1281; Mulligan, 1993, *Science*, 260:926–932, each of which are incorporated herein by reference in their entirety). Exemplary methods of transduction include, e.g., infection employing viral vectors (see, e.g., U.S. Pat. No. 4,405,712 and 4,650,764), calcium phosphate transfection (U.S. Pat. Nos. 4,399,216 and 4,634,665), dextran sulfate transfection, electroporation, lipofection (see, e.g., U.S. Pat. Nos. 4,394,448 and 4,619,794), cytofection, particle bead bombardment, and the like. The heterologous nucleic acid can optionally include sequences which allow for its extra-chromosomal (i.e., episomal) maintenance, or the heterologous nucleic acid can be donor nucleic acid that integrates into the genome of the host.

Host cells contemplated for use in the practice of the present invention include cells well-known in the art in which recombinant production of the invention chimeric proteins can be carried out. As used herein, the phrase "host cell" refers to both prokaryotic and eukaryotic cells, such as mammalian cells (e.g., HEK 293, CHO and Ltk$^-$ cells), yeast cells (e.g., *S. cerevisiae, Candida tropicalis, Hansenula polymorpha, Pichia pastoris* (see U.S. Pat. Nos. 4,882,279, 4,837,148, 4,929,555 and 4,855,231), and the like), bacterial cells (e.g., *Escherichia coli*), insect cells, and the like.

The invention chimeric proteins can be produced by expressing nucleic acid constructs encoding the chimeric proteins in suitable host cells. Methods of producing desired proteins by introducing an expression construct into appropriate cells are well-known in the art.

A preferred method for producing invention chimeric proteins for in vitro use, comprises overexpression of the proteins in bacteria. For overexpression, a T7 polymerase-based system is typically employed. To achieve overexpression, invention nucleic acid constructs encoding the desired chimeric proteins are amplified using primers that add suitable restriction sites to each end of the coding region. The resulting PCR products are cleaved with the appropriate enzymes, and ligated into the T7 expression vector cleaved with the same enzymes. Preferably the pET15b expression vector (commercially available from Novagen) is employed for this purpose, since it directs high level expression and also supplies a His Tag at the amino terminus for convenient purification (see, Bushman et al., 1993, *PNAS, USA*, 83:3428–3432; and U.S. Pat. No. 4,952, 496).

It will be appreciated by the skilled artisan that in some cases it may not be desirable to produce the hybrid protein as a His Tag fusion. Those of skill in the art can remove the His Tag by digestion with thrombin (the pET15b vector adds a thrombin cleavage site between the His Tag and the coding region). A heparin sepharose column can be used for purification of the invention chimeric proteins, since HIV integrase and most DNA-binding proteins bind to heparin sepharose.

Purified invention chimeric proteins can be assayed for the desired integrase activities using suitable oligonucleotide substrates. Sequence specific DNA-binding function of the fused DNA-binding domain can also be assayed by conventional footprinting or band shift assays (Ausubel, et al., 1987, *Current Protocols in Molecular Biology*, Green Publishing Associates and John Wiley and Sons, Inc. USA).

The present invention also relates to a recombinant retrovirus for site-specific integration comprising an invention chimeric protein. As used herein, the term "recombinant retrovirus" refers to a retrovirus that carries an invention chimeric protein within its virion, so that upon infection of a cell, donor nucleic acid within the virion is site-specifically integrated into endogenous genomic DNA.

As used herein, "site-specific" refers to the location of integration of donor nucleic acid within the target nucleic acid. When donor nucleic acid is integrated site-specifically, it is integrated in the immediate vicinity of the region in target nucleic acid which binds the invention chimeric protein.

In one embodiment of the invention, the recombinant retrovirus is an intact replication competent retrovirus that contains a nucleic acid construct encoding an invention chimeric protein within its viral genome. Such retroviruses can be prepared by substituting a nucleic acid encoding an invention chimeric protein for the integrase coding region of a wild-type retroviral genome.

Recombinant retroviruses of the invention are produced employing well-known methods for producing retroviral virions. See, for example, U.S. Pat. No. 4,650,764; Miller, *Human Gene Therapy*, 1:5–14 (1990); Markowitz, et al., *Journal of Viroloqy*, 61 (4) :1120–1124 (1988); Watanabe, et al., *Molecular and Cellular Biology*, 3(12) :2241–2249 (1983); Danos, et al., *Proc. Natl. Acad. Sci.*, 85:6460–6464 (1988); and Bosselman, et al., *Molecular and Cellular Biology*, 7(5):1797–1806 (1987).

Invention recombinant retroviruses capable of targeted integration can be used as insertional mutagens to disrupt deleterious DNA sequences. For example, such retroviruses can be used to inactivate integrated HIV genomes in HIV+ subjects. In addition, HIV recombinant retroviruses capable of targeted integration are useful as attenuated HIV vaccines. For example, previous studies of $SIV_{mac239}$, a close relative of HIV, have established that a mutant derivative can act as an attenuated virus vaccine in macaques (Daniel, M. D. et al. (1992) *Science* 258:1938–1941). The use of such vaccines in humans without the ability to specifically control the location of integration site is potentially very risky, since inoculating a large population with mutant HIV virus would likely cause some cases of disease by insertional mutagenesis. HIV recombinant retrovirus containing an invention chimeric protein (that integrates the viral genome at innocuous sites) substantially reduces the risk.

In another embodiment of the invention, invention recombinant retroviruses are replication incompetent, and contain retroviral vectors that can be site-specifically integrated into a target nucleic acid. Replication incompetent viruses refer to infectious virus particles that after entering a cell, are not able to reproduce infectious particles.

As used herein, "retroviral vector" refers to the well-known gene transfer plasmids that have an expression cassette encoding an heterologous gene residing between two retroviral LTRs. Retroviral vectors typically contain appropriate packaging signals that enable the retroviral vector, or RNA transcribed using the retroviral vector as a template, to be packaged into a viral virion in an appropriate packaging cell line (see, e.g., U.S. Pat. No. 4,650,764).

Suitable retroviral vectors for use herein are described, for example, in U.S. Pat. No. 5,252,479, and in WIPO publications WO 92/07573, WO 90/06997, WO 89/05345, WO 92/05266 and WO 92/14829, incorporated herein by reference, which provide a description of methods for efficiently introducing nucleic acids into human cells using such retroviral vectors. Other retroviral vectors include, for example, the mouse mammary tumor virus vectors (e.g., Shackleford et al., 1988, *PNAS, USA*, 85: 9655–9659), and the like.

Recombinant retroviruses containing an invention chimeric protein within the virion may be prepared by expressing an invention chimeric protein in the packaging cell line used to produce the retrovirus. consequently, any retroviruses produced by these packaging cell lines will contain the invention chimeric protein in the resulting virion providing the integrase function.

Various procedures are also well-known in the art for providing helper cells which produce retroviral vector particles which are essentially free of replicating virus. See, for example, U.S. Pat. No. 4,650,764; Miller, *Human Gene Therapy*, 1:5–14 (1990); Markowitz, et al., *Journal of Virology*, 61(4):1120–1124 (1988); Watanabe, et al., *Molecular and Cellular Biology*, 3(12):2241–2249 (1983); Danos, et al., *Proc. Natl. Acad. Sci.*, 85:6460–6464 (1988); and Bosselman, et al., *Molecular and Cellular Biology*, 7(5):1797–1806 (1987), which disclose procedures for producing viral vectors and helper cells which minimize the chances for producing a viral vector which includes a replicating virus.

Retroviral packaging cell lines that contain a nucleic acid construct encoding an invention chimeric protein are also contemplated herein. Such packaging cell lines may be produced by stably integrating a nucleic acid construct encoding the invention protein into a variety of retroviral packaging cell lines. See, for example, U.S. Pat. No. 4,650,764. The retroviral packaging cells are useful for preparing invention recombinant retroviruses using well-known methods.

Many strategies have been proposed for treating HIV using retroviral vectors. Such strategies include using retroviral vectors to deliver: i) ribozymes that cleave HIV RNA or DNA, ii) dominant negative inhibitors of viral proteins, or iii) cell-specific toxins expressed under the control of a tat-inducible promoter. The safety of these currently available gene therapy protocols can be substantially increased by incorporating an invention chimeric protein into the retroviral virion, thereby directing integration of retroviral vectors to preselected innocuous target sites.

In addition, numerous gene therapy methods, that take advantage of retroviral vectors, for treating a wide variety of diseases are well-known in the art (see, e.g., U.S. Pat. Nos. 4,405,712 and 4,650,764; Friedmann, 1989, *Science*, 244:1275–1281; Mulligan, 1993, *Science*, 260:926–932, each of which are incorporated herein by reference in their entirety). An increasing number of these methods are currently being applied in human clinical trials (Morgan, R., 1993, *BioPharm*, 6(1):32–35). The safety of these currently available gene therapy protocols can be substantially increased by using invention retroviral vectors. In addition, to help overcome the problem of reduced expression from integrated retroviral vectors with time, integration can be directed using invention retroviral vectors to regions adjacent to or near strong tissue-specific promoters.

In accordance with another embodiment of the present invention, there is provided a method for site-specific control of donor nucleic acid integration into target nucleic acid comprising contacting target nucleic acid with an invention chimeric protein, in the presence of donor nucleic acid, under suitable conditions to form a donor-target integration reaction product. As used herein, the phrase "contacting target nucleic acid with a chimeric protein" refers to either the direct or indirect binding of an invention chimeric protein with target nucleic acid.

The contacting step can be achieved extracellularly in vitro. Methods for site-specifically integrating a specified donor nucleic acid in vitro are useful for a variety of applications, such as, for example, for locating and isolating specific genes. Suitable conditions to form a donor-target integration reaction product, extracellularly in vitro, are described, for example, hereinafter.

Alternatively, contacting target nucleic acid with an invention chimeric protein can be carried out intracellularly in vitro, by introducing the chimeric protein into a cell line in which it is desired to site-specifically integrate a donor nucleic acid. The chimeric protein can be contacted with a target nucleic acid intracellularly in vitro by infecting a cell in culture with an invention recombinant retrovirus or retroviral vector that contains a chimeric protein within its virion.

In addition, the contacting of target nucleic acid with chimeric protein can occur intracellularly in vivo, for example, in a mammal. Numerous ways exist for accomplishing such contacting, such as by introducing a recombinant retrovirus containing a chimeric protein within its virion or a retroviral vector encoding the chimeric protein into a cell line in which it is desired to site-specifically integrate a donor nucleic acid.

In accordance with another embodiment of the present invention, there is provided a method for locating specific gene(s) comprising:

contacting target nucleic acid containing regulatory regions associated with specific gene(s) with an invention chimeric protein, in the presence of donor nucleic acid, under suitable conditions to form a donor-target integration reaction product, and detecting the site of integration of said donor nucleic acid.

As used herein, "regulatory region" refers to the region of DNA typically surrounding the gene of interest start site. The regulatory region contains sequences that are recognized and directly bound by specific DNA-binding proteins. As used herein, the phrase "binds to the regulatory region of the gene to be identified" refers to the association (i.e., attaching) of the invention chimeric protein via its first domain to the regulatory region.

For isolating new genes, an invention chimeric protein is used in vitro to isolate sequences from genomic DNA that bind a specified binding domain, e.g., a DNA-binding domain such as that exemplified in an STF-1 transcription factor. The sequences identified by this method are then used as probes to clone the complete gene. It has been found that the lack of expression of the STF-1 transcription factor during mouse embryonic development results in a mouse lacking a pancreas. Genes regulated by STF-1 that are involved in pancreatic development can be located and subsequently isolated employing the invention methods, where the first domain of the invention chimeric protein is derived from, or binds to, STF-1.

To carry out the above method, in vitro reactions containing a donor nucleic acid containing a duplex of oligonucleotides matching in sequence the U5 end region of the unintegrated linear HIV DNA can be used as donor nucleic acid in integration reactions (e.g., FB64 and/or FB65-2, described hereinafter). FB65-2 will also contain a biotin molecule at the 5' end attached during synthesis of the DNA, employing well-known methods, to permit recovery of the integration product.

Genomic target nucleic acid is prepared by shearing the DNA into fragments (e.g., about 0.5 up to about 2 kilobases), and then attaching short oligonucleotide sequences to each end by ligation as described (Sambrook et al., 1989, supra). Following in vitro integration reactions and purification of the integration product, the product DNA is applied to a separation column (e.g., avidin sepharose, Pierce). Only those DNA molecules containing a biotin molecule (i.e., the integration product and the unreacted donor DNA) will bind to the column. After washing, integration product DNA is eluted. The eluted DNA is then amplified using as primers oligonucleotides complementary to the short sequences initially ligated to the genomic DNA fragments. The only amplifiable DNA sequences are those that bound to the column. Amplification yields a pool of genomic DNA fragments enriched in sequences that bind the DNA-binding domain in the invention chimeric protein.

A second-round integration reaction is then repeated as described above, except that the amplification product from the first-round reaction is used as target in the second round. The integration product from the second-round is again purified, amplified, and used as target for a third-round of amplification. This process is repeated as many times as necessary (in the range of 1–25, preferably 5–15) to obtain a pool composed entirely of DNA sequences that bind tightly to the desired DNA-binding domain.

The DNA fragments that emerge as candidate tight binding sequences are cloned into plasmid vectors (Sambrook et al., 1989, supra) and tested for binding to the DNA-binding domain of the respective chimeric protein employed using standard Band Shift or filter binding assays (Ausubel, et al., 1987, Current Protocols in Molecular Biology, Green Publishing Associates and John Wiley and Sons, Inc. USA). It is expected that most or all of the sequences tested will bind tightly to the selected sequences. Those sequences that bind tightly can be further characterized by DNA sequencing, and any common sequences that might constitute binding sites for the DNA-binding protein identified.

Genes that are regulated by the respective DNA-binding domain are isolated using the above tight binding sequences as probes. It is expected that many of the tight binding sites will lie in the promoters (i.e., regulatory region) of genes controlled by the DNA-binding protein. Larger DNA fragments potentially containing the coding region of the new genes are isolated by screening libraries of human DNA using the newly cloned sequences as probes. Screening of phage plaques by hybridization is carried out by using well-known methods. Transcript mapping and DNA sequencing are employed to reveal the location of genes regulated by the new DNA binding protein (Sambrook et al., 1989, supra). Once the gene is located, the isolation of cDNAS corresponding to the newly located gene is well within the skill in the art.

All U.S. and Foreign Patent publications, textbooks, and journal publications referred to herein are hereby expressly incorporated by reference in their entirety. The invention will now be described in greater detail by reference to the following non-limiting examples.

EXAMPLE 1

Preparation of Nucleic Acid Constructs Encoding Invention λR-IN Chimeric Protein.

A model invention chimeric protein (λR-IN) containing a fusion of the DNA binding domain of λ repressor to integrase was prepared by constructing a plasmid encoding the modified protein. Procedures for manipulating DNA molecules were essentially as described (Sambrook et al., 1989, supra). A plasmid encoding the amino terminal domain of λ repressor fused to the leucine zipper of GCN4 (pJH370) served as the cloning vector (Hu et al., 1990, Science, 250:1400–1403). Expression of the encoded fusion protein was controlled by the lac UV5 promoter. To remove an interfering Nde I restriction enzyme recognition site from the plasmid pJH370, a Pst I to Bsa AI fragment from pET15b (Novagen, Madison, Wis.) was substituted for the corresponding fragment in pJH370, yielding pFB257. This plasmid was then cleaved with Nde I and Bam HI, and ligated with a Nde I to Bam HI fragment encoding full length (amino acids 1–288) HIV-1 integrase described previously (Bushman et al., 1993, PNAS, USA, 90:3428–3432). The resulting λ repressor-integrase fusion plasmid encoding the invention λR-IN chimeric protein (containing λ repressor amino-terminal to integrase) was designated pFB258. The nucleotide sequence at the junction of the invention chimeric protein indicated that DNA-binding domain and the integrase domain were in the same reading frame (SEQ ID NO:10):

```
       A  E  R  W  V  S  T  H  M  F  L  D  G
5' GCGGAGAGATGGGTGTCGACACATATGTTTTTAGATGGA 3'.
```

EXAMPLE 2

Expression and Isolation of an Invention λR-IN Chimeric Protein.

The λR-IN chimeric protein was assayed throughout the purification by Western blotting using a rabbit polyclonal antisera raised against HIV integrase. E. coli strain AG1688 (MC1061 F'128 lacI$^Q$ lacZ::Tn5) was doubly transformed with plasmid pFB258 and pMS421 (which supplies a high level of lac repressor) (Grana et al., 1988, Genetics, 120:319–327). Cultures were grown in Terrific Broth (Sambrook et al., supra), and induced at mid-log phase by adding 1 mM IPTG. Cells were harvested by centrifugation, and resuspended in 0.5 M NaCl, 20 mM Tris pH8, 0.1 mM EDTA. Cells were lysed by i) freezing in liquid nitrogen and thawing at 37° C., ii) incubation with 0.2 mg/ml lysozyme, and iii) sonication. The lysate was centrifuged for 30 min. at 44,000×g. The λR-IN protein was extracted from the insoluble fraction with 1 M NaCl, 20 mM Hepes pH7.5, 0.1 Mm EDTA, 1 mM DTT (Buffer A).

The extracted material was precipitated with ammonium sulfate, and the precipitate was collected by centrifugation. The precipitate was extracted sequentially with Buffer A+20% Ammonium Sulfate, and then Buffer A alone. The λR-IN protein, which is quite insoluble in ammonium sulfate, was highly enriched in the supernatant of the extraction with Buffer A. This material was dialyzed against Buffer A, and then diluted to 50 mM NaCl with 20 mM Hepes pH7.5, 0.1 mM EDTA, and 1 mM DTT. The diluted material was applied to a heparin sepharose column, and eluted with a linear 50 mM NaCl to 1M NaCl gradient in 20 mM Hepes pH7.5, 0.1 mM EDTA, and 1 mM DTT. Fractions containing the λR-IN protein were pooled, dialyzed against Buffer A+10% glycerol, and used for integration assays. The protein concentration was determined from the UV spectrum.

EXAMPLE 3

In Vitro Integration Assays Utilizing Invention λR-IN Chimeric Proteins.

The operator binding and catalytic activities of the hybrid were first assayed independently. Once these activities were confirmed to be present, target site selection by λR-IN was examined.

Several oligonucleotides matching in sequence the U5 end region of the unintegrated linear viral DNA were used as donor nucleic acids in integration reactions. U5-1, used in Example 3B, consists of two oligonucleotides of sequence 5'ACTGCTAGAGATTTTCCACACGGATCCTAGGC 3' (FB64/SEQ ID NO:1) and 5'GCCTAGGATCCGTGTC-GAAAATCTCTAGCATG 3' (FB65/SEQ ID NO:2). U5-2, used in Example 3C, consists of a single oligonucleotide hairpin of sequence 5 'ACTGCTAGAGATTTTCCACACG-GATCCTAGGCTTTTGCCTAGGATCCGT-GTGGAAAATCTCTAGCA 3' (FB79/SEQ ID NO: 3). Both the removal of the two nucleotides normally removed by integrase and the linking of the two strands by a hairpin increased the amount of product recovered in test reactions. U5-3, used in Example 3E, is identical to U5-1 except the two 3' nucleotides of FB65/SEQ ID NO: 2 have been removed (yielding FB65-2). Substrates were labeled by treatment of FB65/SEQ ID NO: 2 or FB79/SEQ ID NO: 3 with γ-32P ATP and T4 polynucleotide kinase prior to hybridization using well-known methods.

Integration reactions contained 5 mM $MnCl_2$, 25 mM Hepes pH7.5, 20 mM BME, 100 μg/ml BSA, 10% glycerol, and 0.2 pmol U5-1 donor oligonucleotide in 20 μl final volume. For assays of activity on oligonucleotide substrates, integrase or λR-IN was added last to test reactions. Assays were incubated for 1 hr. at 37° C., and then stopped by adding sequencing gel loading dye containing excess EDTA, and heating the mix at 95° C. for 3–5 min. Reaction products containing donor nucleic acid integrated into target nucleic acid were separated by electrophoresis on a 15% polyacrylamide DNA sequencing-type gel, and were visualized by autoradiography.

For assays of integration into λ DNA targets, 2.5 μg of phage λ DNA (cI857 ind1 Sam7, New England Biolabs) cut with the indicated restriction enzyme was added to each reaction. Integrase or λR-IN was preincubated with target on ice for 20 min., and reactions were started by adding the U5-2 donor DNA and incubating the reaction mixture at 37° C. for 30 min.

A. Binding of λR-IN to λ Operators.

λR-IN was tested for the ability to bind λ operators. λR-IN contained residues 1–133 of λ repressor, a region encompassing the DNA-binding domain. A genetic assay was used to monitor binding of the hybrid protein to λ operators. *E. coli* cells expressing each protein were exposed to λ phage. Those cells that contained proteins Capable of binding to λ operators were immune to infection and so capable of growth, while those cells containing proteins incapable of binding were lysed by the phage. Immunity was assayed by a cross streaking test. Phage lysate (25 μl) was streaked vertically on an LB plate and allowed to dry. Next, E. coli (MC1061 F'128 lacI$^Q$ lacZ::Tn5) containing plasmids directing the expression of the indicated proteins were streaked horizontally. In addition to the plasmid directing the expression of the fusion protein, cells contained a second compatible plasmid, pMS421 (Grana et al., 1988, *Genetics*, 120:319–327), that supplied a high level of lac repressor. Expression of the fusion proteins was directed by the lacUV5 promoter, which could be turned off by lac repressor. LB plates contained 10 uM IPTG, a concentration sufficient to partially but not fully induce the lac promoter. Plates also contained 100 μg/ml ampicillin and 100 μg/ml spectinomycin to select for the two plasmids.

Cell death at the phage streak indicated that the cells were sensitive to infection, survival indicated immunity. The phage used in this test, λKH54, contains a deletion in cI, the repressor gene, and so grows lytically on sensitive cells.

The gene encoding λR-IN fusion protein was cloned on a plasmid so that expression in E. coli was directed by the lacUV5 promoter. Immunity was assayed in the presence of different amounts of the fusion protein by varying the amount of IPTG in the assay plates. In the presence of 10 μM IPTG, cells expressing λ repressor 1–133 only were sensitive to infection by λKH54. Cells containing λR$^{1-133}$ fused to the complete HIV integrase ($IN^{1-288}$) were immune to λKH54 indicating that the λ-repressor domain is a functional DNA-binding domain in the chimeric protein.

B. DNA Cleavage and Integration Activities of λR-IN

λR-IN was purified and tested for the known activities of HIV-1 integrase. Prior to the integration of retroviral DNA, integrase removes 2 nucleotides from each 3' end of the viral DNA. Purified integrase is capable of carrying out this terminal cleavage reaction in vitro on oligonucleotide substrates that model one end of the viral DNA (FIG. 1b). For this assay, a thirty base pair model viral DNA (U5-1) was labeled on one 5'-end with $^{32}P$, and then incubated with integrase or λR-IN in the presence of $Mn^{2+}$. Reactions containing both wild-type integrase and λR-IN yielded the expected terminal cleavage product. λR-IN was also able to integrate the recessed 3' end produced in this reaction into oligonucleotide target DNAs.

C. Integration Site Selection by λR-IN

To examine integration into DNA containing λ operators, test reactions were carried out in which phage λ DNA was used as an integration target nucleic acid. λ DNA contains two groups of repressor binding sites, the right and left operators ($O_R$ and $O_L$). Target λ DNA was cleaved with Eco RI, yielding a fragment of 7.4 kb containing $O_L$ and $O_R$ and 5 other fragments lacking operators that served as controls. Purified HIV IN or λR-IN was preincubated with 2.5 μg of Eco RI-cleaved λ DNA, and integration reactions were started by adding the end-labeled viral end substrate (U5-2/SEQ ID NO:3). After incubation for 30 min. at 37° C., reactions were stopped and DNA products were analyzed by electrophoresis on native agarose gels. Integration products were visualized by autoradiography and total λ DNA was visualized by staining with ethidium bromide. The unincorporated viral end substrate was not retained on the gel due to its short size. Because the model viral end is much shorter than the λ target DNA fragments, integration of the viral end does not result in a detectable change in the mobility of the integration product. The observation that the target DNAs retain the mobility of the unreacted target fragment implies that both wild-type integrase and λR-IN are integrating primarily single viral DNA ends into the target nucleic acid, yielding Y-shaped strand transfer products (FIG. 1b, bottom).

Reactions containing wild-type integrase yielded signals at each of the λ DNA fragments. The intensity of the signal is roughly proportional to the mass of target DNA present. Reducing the amount of integrase reduced the signal, but did not alter the relative signals of each fragment. Integration signals from reactions containing 16 pmol of λR-IN, in contrast, were unevenly distributed, with integration favored in the fragment containing $O_L$ and $O_R$. Reactions containing less of the λR-IN protein yielded less total integration product, but the $O_L$-$O_R$ fragment contained an even greater proportion of the total integration signal. This response is consistent with the view that 16 pmol of the λR-IN protein represents a functional excess of active multimers over operator sites, while the lower amounts of λR-IN fail to saturate the operator sites.

λR-IN also directed integration into operator-containing DNA fragments in experiments in which the target λ DNA was cleaved with other restriction enzymes. Cleavage of λ DNA with Bst EII yields separate DNA fragments containing $O_L$ and $O_R$. Products of integration reactions containing wild-type integrase display similar autoradiographic signals at each λ DNA band. Products of reactions containing λR-IN, in contrast, display stronger signals at the fragments containing $O_L$ and $O_R$. The bias is again most pronounced at the lowest concentration of the λR-IN fusion. Experiments containing λ DNA cleaved with Sma I or Nco I yielded similar results. Cleavage of λ DNA with these two enzymes yielded single fragments containing $O_L$ and $O_R$, and again integration by λR-IN was preferentially directed to the fragment containing the operators.

D. Competition of Site Specific Integration by Phage Repressors

Competition experiments were carried out to test the idea that selective integration by the λR-IN fusion was mediated by binding to λ operators. If λR-IN was binding to λ operators, then prebinding λ repressor to those same sites should block selective integration. Target DNA was preincubated with repressor for 5 min. on ice, integrase or λR-IN was added and incubated 5 min. on ice, and then reactions were started by adding the U5 donor oligonucleotide and transferring the reaction mix to 37° C. Reactions were stopped after 20 min. by adding excess EDTA, SDS to 0.1%, and one fifth volume native gel loading dye. Reaction mixtures were heated at 60° C. for 3 min. (to melt the annealed λ DNA cohesive ends) and resolved on a 0.7% TAE agarose gel. Following electrophoresis, bulk DNA was visualized by staining with ethidium bromide. The gels were then dried, and reactions products were visualized by autoradiography.

In the products of integration into λ DNA cleaved with Bst EII generated by 11 pmol of λR-IN, integration is favored in those fragments containing $O_L$ and $O_R$, but lower levels of integration into other fragments is also detectable. Addition of 0.7–2 pmol of λ repressor has little effect. Upon addition of 6 pmol repressor, however, the pattern of site selection is changed such that integration events are evenly distributed on the target DNA. For the case of wild-type integrase, integration sites were evenly distributed over all the DNA fragments, and addition of repressor did not change this pattern.

As a control, the experiment was repeated using the repressor protein of the heteroimmune lambdoid phage 434 as competitor. Phage 434 repressor acts at the 434 right operator in a manner closely similar to that described for λ repressor, but 434 repressor binds specifically only to 434 operators. Titration of 434 repressor into integration reactions containing a λ DNA target and λR-IN or wild-type integrase did not influence the selection of integration target. These data support the view that the λR-IN fusion directs integration specifically into λ DNA fragments containing $O_L$ and $O_R$ by binding to λ operators.

E. High Resolution Analysis of Integration Sites in $O_R$.

Figure 4:
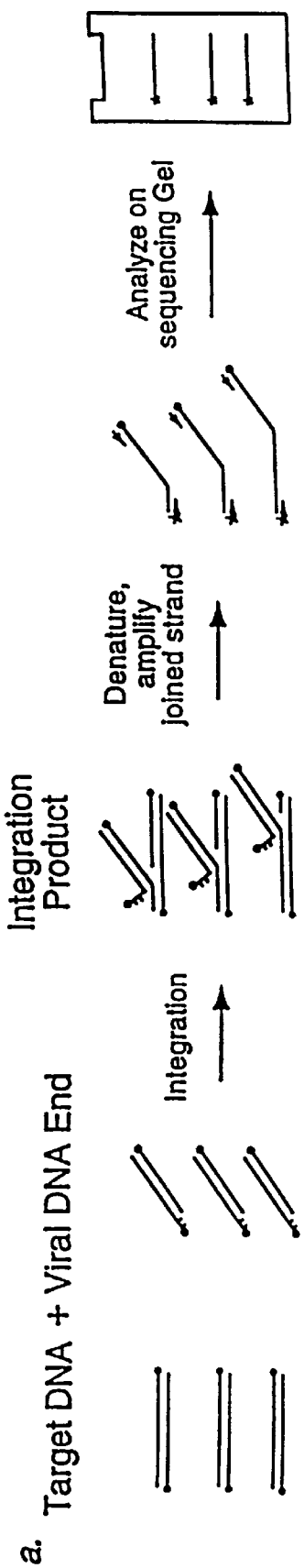
FIG. 4 depicts a diagram of the PCR-based method used for high resolution mapping of integration sites.

Integration reactions for analysis of products by PCR were carried out as above in Examples 3C and 3D, except U5-3 was used as the oligonucleotide donor and none of the DNA substrates were $^{32}P$ labeled. Reactions were stopped as above (except native gel loading dye was not added), deproteinized by phenol extraction and ethanol precipitation, and resuspended in 20 μl of TE. Each PCR reaction contained one primer (FB66/SEQ ID NO: 4; sequence: 5' GCCTAGGATCCGTGTGGAAAATC 3') complementary to the U5-3 donor oligonucleotide and a second primer complementary to λ DNA near the right operator. Two target primers were used in separate reactions, each complementary to one of the DNA strands. FB182/SEQ ID NO:5; 5'GACAGATTCCTGGGATAAGCCAAG3', λ nucleotides 37830 to 37853; FB183/SEQ ID NO: 6: 5' CGCGCTTTGATATACGCCGAGATC 3', λ nucleotides 38104 to 38127. FB182/SEQ ID NO: 5 and FB183/SEQ ID NO: 6 were labeled prior to use as PCR primers by treatment with $\gamma^{32}P$ ATP and T4 polynucleotide kinase. PCR reactions contained 4 μl of integration product, 0.2 μl of each primer (FB66/SEQ ID NO: 4 and either FB182/SEQ ID NO.: 5 or FB183/SEQ ID NO: 6) 0.25 mM each dNTP, 1X Taq Buffer (Stratagene), 0.1 mg/ml BSA, and 2.5 units Taq polymerase (Stratagene) in a final volume of 50 μl. Reactions were overlaid with paraffin oil and subjected to thirty cycles of amplification at 95° C. for 1 min., 55° C. for 1 min., and 72° C. for 2 min. A final extension at 72° C. for 10 min. was also included. Following amplification, reactions were extracted once with CHCl$_3$, and aliquots were mixed with 2 volumes of denaturing gel loading dye, heated at 95° C. for 3–5 min., and loaded on a 6% denaturing DNA sequencing-type gel. Labeled products were visualized by autoradiography, and results were quantitated using a Molecular Dynamics PhosphorImager. The above assay, shown schematically as FIG. 4, is described in Kitamura et al. (1992), *PNAS, USA*, 89:5531–5536; and Pryciak and Varmus (1992), *Cell*, 69:769–780.

A close examination of the integration sites used by the invention λR-IN chimeric protein revealed that integration sites cluster near the operators and progressively diminish in use as one proceeds along the DNA away from the operators. Titrating λ repressor into reactions containing λR-IN diminishes integration into the sites near $O_R$. These data are consistent with a model in which integration near $O_R$ is carried out by the λR-IN fusion protein bound at $O_R$.

EXAMPLE 4

Construction of a Recombinant Retrovirus and Assays for in vivo Integration and Replication These experiments established that integrase can tolerate the addition of 19 amino acids to the carboxyl-terminus and retain clear function in the context of a replicating retrovirus in vivo. The construction of this fusion by adding a His Tag (HT) and a hemagglutinin epitope tag (HA) to integrase is also useful to simplify the purification of HIV-1 preintegration complexes. The pNL4-3 provirus (Adachi et al., 1986, *J. Virol.* 59:284–291) was chosen for use in this study for consistency, since the ihtegrase coding region used in the in vitro experiments was derived from pNL4-3. R8 is a plasmid containing the pNL4-3 protein coding regions in the context of a replication-competent provirus. R8 was derived from the R7 base plasmid (also referred to as plasmid "WI3"; Kims et al., 1989, *J. Virol.*, 63:3708–3713) by ligating the Bam HI-Bss HII restriction fragment of plasmid pNL4-3 into the R7 plasmid cleaved with the same enzymes.

Figure 3:
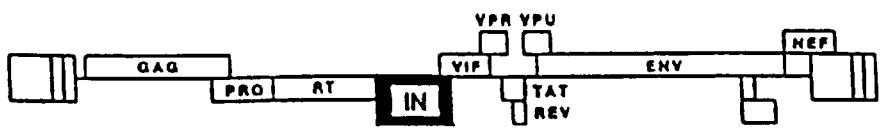
FIG. 3 depicts genetic maps of wild-type HIV and engineered derivatives.
Figure 3:
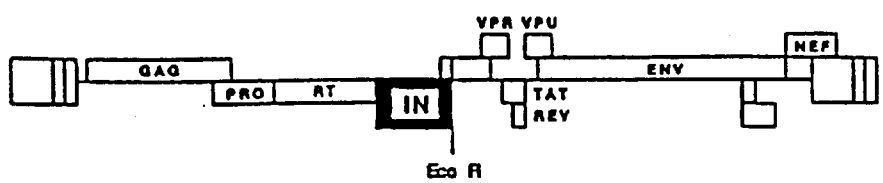
Figure 3:
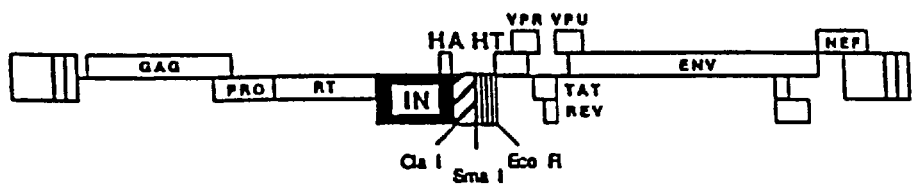
Figure 3:
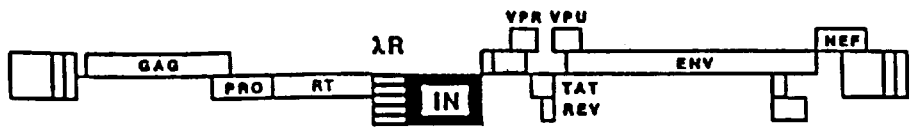
Figure 3:
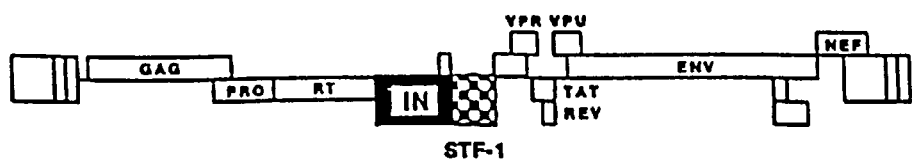

For the construction of the integrase-HAHT chimeric, PCR was first employed to generate an intermediate DNA construction that placed a restriction site at the end of the integrase coding region (R8Vif-). To insert the HA and HT tags, a duplex oligonucleotide encoding those sequences was cloned into R8Vif-, generating R8Vif-HAHT (FIG. 3). Purified integrase containing this fusion bound to a Ni-chelating column and the fusion protein displayed the expected terminal cleavage and strand transfer activities.

The abilities of the R8Vif- and R8Vif-HAHT encoded viruses to carry out the early stages of HIV replication was measured by a MAGIC assay (Kimpton et al., 1992, *J. Virol.*, 66:2232–2239). Cells from the 293 cell line (ATCC accession #CRL-1573) were transfected with R8 (the wild-type starting plasmid), R8Vif-, R8Vif-HAHT, E152A (a strong integrase mutant) or no DNA. After 24 hr., culture supernatants were harvested, filtered, and used to infect p4-2 cells (i.e., H12 cells, Charneau et al., 1992, *J. Virol.*, 66:2814–2820). The p4-2 cells contain a β-galactosidase gene under the control of an HIV LTR. The β-galactosidase coding region is modified so as to contain a nuclear localization signal. Integration of an HIV provirus into these cells has two effects: i) it permits expression of β-galactosidase by providing Tat protein and ii) it directs the formation of syncytia. The activity of a viral preparation can thus be quantitated by counting the number of syncytia with blue nuclei. Such counts for R8Vif- and R8Vif-HAHT are within 50% of the wild-type control (Table 1).

TABLE 1

MAGIC Assay of R8 and Derivatives

| Virus | Bluefoci/ng p24 |
| --- | --- |
| R8 | 62 |
| R8Vif- | 90 |
| R8Vif-HAHT | 47 |
| E152A (integrase mutant) | 0 |
| no virus | 0 |

In addition, we find that these viruses are able to spread in SupT1 cells (Smith et al., 1984, *Cancer Res.*, 44:5657). These data indicate that the fusion of 19 amino acids to the carboxyl-terminus of integrase does not block the integrase function. Besides establishing the operability of building integrase fusions into replicating HIV derivatives, the DNA constructs developed in this work provide convenient vectors in which to clone further integrase fusions (as described hereinafter).

EXAMPLE 5

Construction of Recombinant Retroviral Proviruses Encoding Invention Chimeric Proteins FIG. 3 depicts genetic maps of wild-type HIV and engineered derivatives. R8Vif-λR-IN is a derivative of R8Vif- encoding a fusion of λ repressor (residues 1–133, horizontal stripes) to the amino terminus of integrase. R8Vif-IN-STF is a derivative of R8Vif-HAHT encoding the homeodomain of STF-1 (checkered) linked to the carboxyl-terminus of integrase. DNA constructions encoding each of these viruses have been made.

A. λR-IN Recombinant Retrovirus

DNA encoding the λR-IN fusion was amplified from pFB258 (i.e., the prokaryotic expression vector encoding λR-IN described in Example 1). The primer to the carboxyl-terminal side of the coding region added a Cla I restriction enzyme recognition site. When a first domain is fused amino-terminal to integrase in a viral genome, a suitable protease site is incorporated immediately upstream, amino-terminal to the first domain to allow proper proteolytic processing. The primer on the amino-terminal side added sequences encoding a novel protease (i.e., amino acids—NFPQ) recognition site and homology to the carboxyl-terminus of RNase H (SEQ ID NO:9):

Separately, the region of HIV encoding reverse transcriptase and RNase H was amplified. The primer to the 3' side encoded sequences complementary to the carboxyl-terminus of RNAse H and the novel protease recognition site . In a second round, PCR products from each of the first rounds were mixed and amplified in the presence of the two "outside" primers. This resulted in the precise fusion of the two fragments, and subsequent amplification of the fusion fragment (Vallette, et al., 1989, *NAR*, 17:723–733; and Yon and Fried, 1989, *NAR*, 17:4895). This DNA was then isolated, cleaved with Bcl I and Cla I, and ligated with the R8Vif-HAHT proviral clone that had been cleaved with Bcl I and Cla I. The desired ligation product (R8Vif-λR-IN in FIG. 3) was identified by restriction enzyme digestion and characterized by DNA sequencing.

B. IN-STF-1 Recombinant Retrovirus

A cDNA encoding the STF-1 homeodomain was used as a template for PCR. Primers were designed to add a Cla I site to the 5' side FB 188/SEQ ID NO:7) and a Sma I site to the 3' side (FB 189/SEQ ID NO:8) of the coding region for the 76 amino acid DNA-binding domain of STF-1 (corresponding to a.a. 140–215 described in Leonard et al., 1993, *Mol. Endo.*, 7:1275–1283):

```
FB 188 - 5' GCCGAAGCATCGATGCAGCAGAACCGGAGGAGAATAAG 3'
FB 189 - 3' TTTGCATCATCGCCCTGTTGCTCGACTGGGCCCTACGTGGC 5'.
```

The resulting PCR fragment was cleaved with Cla I and Sma I, and ligated to R8Vif-HAHT cleaved with Cla I and Sma I. The desired recombinants were characterized by restriction mapping and DNA sequencing. These manipulations resulted of the attachment of the STF-1 coding region for the 76 amino acid DNA-binding domain in frame at the carboxyl-terminus of integrase (R8Vif-IN-STF in FIG. 3).

C. IN-zif268 Recombinant Rretrovirus

The zif268 zinc finger domain can be fused to the carboxyl-terminus of integrase in the R8Vif-HAHT vector (FIG. 3) essentially as described above in Example 5B. As discussed above with respect to modification of existing DNA-binding domains, such a virus may potentially be modified to direct integration into many different predetermined sequences.

EXAMPLE 6

Characterizing Invention Retroviral Vectors and Recombinant Retroviruses

A. Assay for Intracellular Integration Competence of R8Vif-λR-IN

Viral stocks were made by transfecting 293 cells with plasmids encoding the R8Vif-λR-IN recombinant retrovirus and harvesting supernatants containing virus two days later. The amount of virus produced was determined by measuring the concentration of a viral antigen (p24) in the supernatants. A known amount of virus was then used to infect P4-2 indicator cells. Infectious centers were measured as in the standard MAGIC assay (Kimpton, J., and Emerman, M. (1992), *J. Virol.* 66:2232–2239). The results of the assay (shown in Table 2) indicate that the HIV derivative Vif-λR-IN recombinant retrovirus is competent for integration.

```
5 'AGTGCTGGAATCAGGAAAGTACTAAACTTTCCGCAGATGAGCACAAAAAAGAAAC
CATTA 3'.
```

TABLE 2

| Virus | Infectious centers/ng24 | Comments |
|---|---|---|
| R8 | 420 | Wild Type HIV |
| R8Vif-λR-IN | 25 | Contains λR-IN |
| E152A | 0 | Strong integrase mutant |

B. Assay for Replication Competence

Viral stocks are generated by transfecting 293 cells with cloned invention retroviral vectors (i.e., proviral derivatives) and culture supernatants are collected. Viral stocks are standardized by measuring the concentration of p24 antigen in each. The stocks are then applied to p4-2 cells (Kimpton and Emerman, 1992, *J. Virol.*, 66:2232–2239), which allow infectious units to be scored as β-galactosidase positive syncytia (MAGIC assay). Supernatants are also added to target cells such as SupT1 at low multiplicity of infection and the amount of p24 antigen is measured as a function of time. As appropriate, the growth curves are also characterized by measuring reverse transcriptase activity and viral nucleic acids produced as a function of time. If any of the mutants grow with delayed kinetics, stocks from these cultures are applied to fresh cells to check whether such late appearing viruses replicate with wild-type kinetics, indicating reversion. As appropriate, the viral sequences are amplified by PCR from the virion RNA and sequenced to confirm the integrity of the fusion.

C. Assay for the Processing and Abundance of Recombinant Retroviral Proteins

Viral particles are concentrated from culture supernatants by centrifugation at 23,000 RPM for 2.5 hr. in an SW28 rotor, and aliquots are boiled in SDS-PAGE loading dye. Viral lysates are then analyzed by Western blotting using, e.g., antisera against integrase or total viral proteins. This analysis allows confirmation that invention chimeric proteins are present in virions and that viral proteins are properly processed.

EXAMPLE 7
Modification of Existing DNA-Binding Domains to Recognize New Target Recognition Sequences A. Zinc Finger Modification Modification of existing DNA-binding domains expands the utility of the invention by permitting the recognition many new sequences. Many zinc finger proteins consist of several tandem finger repeats. In some of these roteins each finger recognizes three adjacent DNA bases (Desjarlais and Berg, 1993, *PNAS, USA*, 90:2256–2260; and Pavletich and Pabo, 1991, *Science*, 252:809). It has been found that these zinc fingers can be "mixed and matched" to yield new DNA binding specificities. For example, several zinc finger proteins containing the same three zinc fingers, but in rearranged order have been prepared (Desjarlais and Berg, 1993, *PNAS. USA*, 90:2256–2260). The modified proteins recognized the same 9 base pair sites, but with the three base pair units rearranged in the predicted order. Thus, new specificities can be created by rearranging the order of zinc fingers in multi-finger proteins.

In addition, new DNA-binding specificities have been conferred on individual $Cys_2$-$His_2$ fingers (Rebar and Pabo, 1994, *Science*, 263:671–673). For example, phage display libraries have been used to isolate new fingers that recognize a preselected sequence from a library containing randomized recognition sequences. The zif-268 finger protein, which contains three zinc fingers, was randomized in the amino acids of one finger involved in DNA-contacting, and was expressed on the surface of a bacteriophage. Phage capable of binding a mutant DNA site were isolated by applying the phage display library to a dish coated with the DNA site of interest. After washing, bound phage were eluted with high salt and grown up. The selection was then repeated several more times, using as starting material for the next round the phage recovered from the previous round. At the end of this procedure, the remaining phage encoded zif268 derivatives with high affinities for the new DNA sequences. Those of skill in the art will recognize that combining the ability to evolve individual fingers to recognize new sites with the ability to mix and match different fingers allows the design of zinc finger proteins that recognize any DNA sequence.

B. Zif268 DNA-Binding Domain Modification to Recognize an L1 Element

L1 element DNA is an attractive binding domain recognition site because disruptions in such sequences are known to be harmless. The zif268 protein can be modified to bind to the sequence 5'GGGGCAGGG3', which is found near the 3' end of L1 elements (Hattori et al., 1985, *NAR*, 13:7813–7827). By following the rules of Desjarlais and Berg (Desjarlais and Berg, 1993, *PNAS, USA*, 90:2256–2260), and using a new recognition element from the work of Rebar and Pabo (Rebar and Pabo, 1994, *Science*, 263:671–673), a new specificity is designed to recognize this L1 sequence. Specifically, changing the critical recognition amino acids in the three fingers (13, 16, and 19 in each finger according to the numbering of Desjarlais and Berg) to contain the sequence RHR (finger 1), QGS (finger 2) , and RHR (finger 3) produces a protein that recognizes the desired L1 sequence.

C. Modification of the Hin DNA-Binding Domain to Recognize an L1 Element

When a relatively small DNA-binding domain is desired (e.g. approximately 50 amino acids), directed in vitro evolution may be employed to modify the 52 amino acid Hin DNA-binding domain to recognize the L1 sequence or other desired sequences. For example, DNA encoding the Hin DNA-binding domain can be cloned into the fUSE2 vector (Parmley and Smith, 1988, *Gene*, 73:305–318), and selections carried out using the methods of Rebar and Pabo described above.

EXAMPLE 8
Preparation of a Protein-Binding Domain that Indirectly Attaches to Target Nucleic Acid by Binding to STF-1

To produce a protein-binding first domain of an invention chimeric protein that binds to STF-1, the phage display library method is used to create an approximately 19 amino acid peptide that binds tightly to STF-1. The STF-1 protein-binding domain peptide is then fused to integrase to form an invention chimeric protein (as described hereinafter). The integrase-STF-1 protein-binding domain chimeric protein is assayed (as described herein) to determine whether it targets integration to DNA bound to STF-1 in vitro. This chimeric protein is also incorporated into a recombinant retrovirus (as described in Example 5) and tested intracellularly in cells expressing STF-1 (e.g., pancreas-derived cells).

Figure 2:
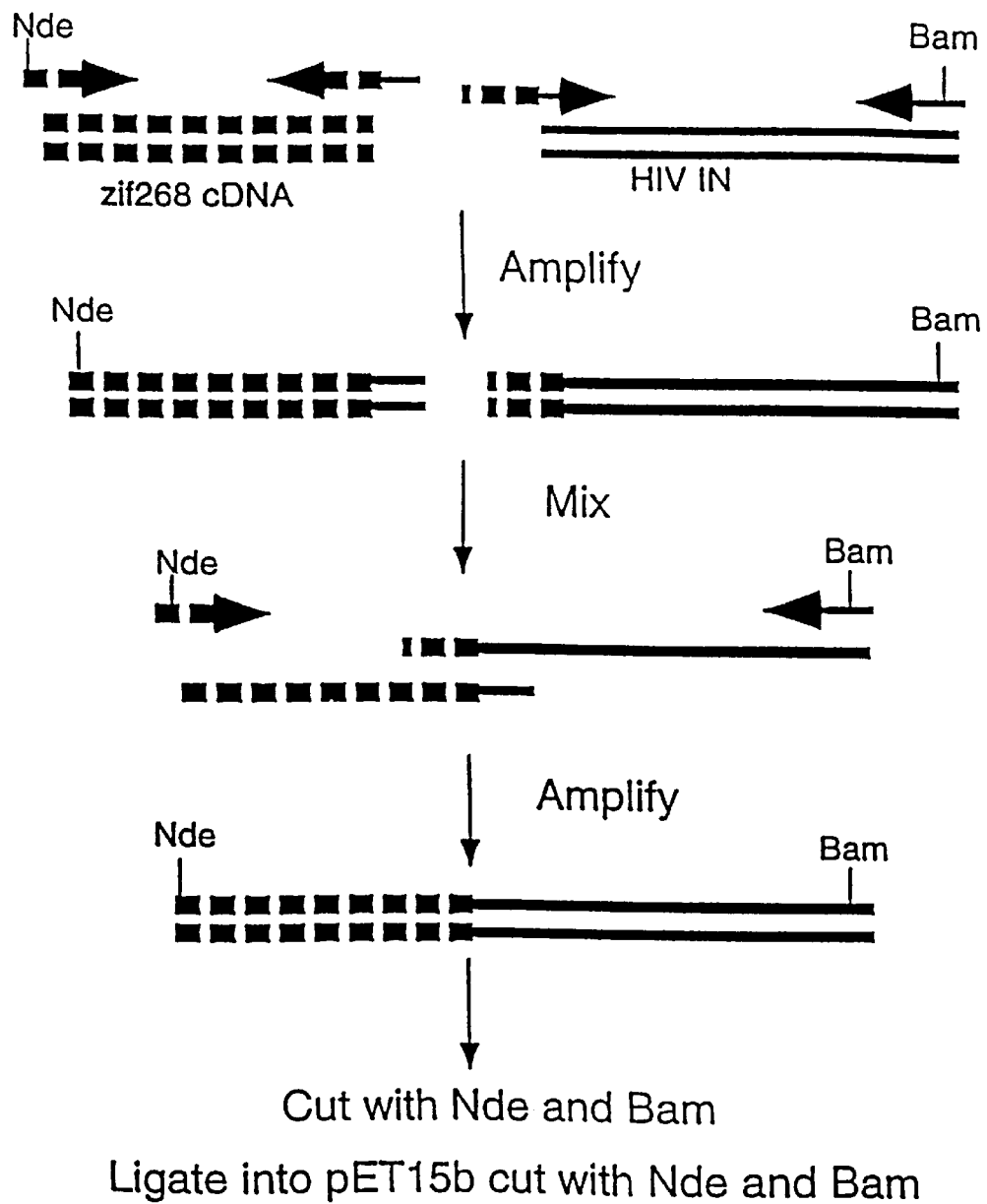
FIG. 2 depicts the construction of an invention nucleic acid construct encoding a zif268-IN, chimeric protein employing the polymerase chain reaction (PCR).

EXAMPLE 9
Preparation of Nucleic Acid Constructs Encoding Invention Chimeric Proteins Invention chimeric proteins containing the DNA-binding domain "amino-terminal" to the integrase domain are constructed using fusion PCR (see, e.g., Vallette, et al., 1989, *NAR*, 17:723–733; and Yon and Fried, 1989, *NAR*, 17:4895). For example, FIG. 2 illustrates the construction of a DNA constructing encoding zif268 fused to the amino terminus of HIV-1 integrase. The integrase coding region and the zif268 coding region are separately amplified by PCR. Primers are designed employing well-known methods to contain a region of overlap that encodes the desired fusion junction. PCR products from the two separate reactions are then purified, mixed, and subjected to a second PCR reaction using primers directed at either side of the overlap region. In the first cycle of the second round, strands from the two reaction products can denature and anneal to allow extension by the polymerase. In the next cycle, the resulting strand can be amplified as in normal PCR. Thus two unrelated sequences can be precisely fused.

Chimeric proteins containing the DNA-binding domain "carboxyl-terminal" to the integrase domain can be constructed by cloning sequences encoding DNA-binding domains into the retroviral vector R8Vif HAHT described in Example 4.

While the invention has been described in detail with reference to certain preferred embodiments thereof, it will be understood that modifications and variations are within the spirit and scope of that which is described and claimed.

That which is claimed is:

1. A chimeric protein comprising:
   a first domain, which domain comprises a sequence-specific DNA-binding domain or which domain comprises a protein-binding domain which indirectly attaches said chimeric protein to a specific recognition sequence of a nucleic acid through attachment of said protein-binding domain to at least one other protein which facilitates attachment of said chimeric protein to said specific recognition sequence of a nucleic acid; and
   a second domain, which domain comprises an integrase protein or a fragment of said integrase protein which integrates donor nucleic acid into target nucleic acid,
   wherein the first domain is heterologous to the second domain and the carboxyl terminus of the first domain is joined to the amino terminus of the second domain or the carboxyl terminus of the second domain is joined to the amino terminus of the first domain.

2. A chimeric protein according to claim 1, wherein said sequence-specific DNA-binding domain is a sequence-specific DNA-binding domain from a transcription control protein, a recombination enzyme or a site-specific DNA-modifying enzyme.

3. A chimeric protein according to claim 1, wherein said integrase protein is a retroviral integrase.

4. A chimeric protein according to claim 1, wherein said integrase protein is selected from the group consisting of human immunodeficiency virus-1 integrase, human immunodeficiency virus-2 integrase, human T-cell leukemia virus, feline immunodeficiency virus integrase, simian immunodeficiency virus integrase, Rous sarcoma virus integrase, human foamy virus integrase, and Moloney murine leukemia virus integrase.

5. A chimeric protein according to claim 1, wherein said integrase protein is a human immunodeficiency virus-1 integrase.

6. A chimeric protein according to claim 1, wherein the carboxyl terminus of the first domain is joined to the amino terminus of the second domain.

7. A chimeric protein according to claim 1, wherein the carboxyl terminus of the second domain is joined to the amino terminus of the first domain.

8. A method for site-specific control of donor nucleic acid integration into target nucleic acid comprising contacting said target nucleic acid with the chimeric protein according to claim 1 in the presence of said donor nucleic acid, under conditions wherein a donor-target integration reaction product is formed.

9. A method according to claim 8, wherein said donor nucleic acid comprises at least one end region of a retroviral long terminal repeat.

10. A method according to claim 9, wherein said donor nucleic acid comprises two retroviral long terminal repeats.

11. A method according to claim 10, wherein said donor nucleic acid is a retroviral vector.

12. A method according to claim 8, wherein said contacting occurs intracellularly.

13. A method according to claim 8, wherein said contacting occurs extracellularly.

14. A method for locating a gene comprising:
   contacting a target nucleic acid containing a regulatory region associated with said gene, with the chimeric protein according to claim 1 in the presence of a donor nucleic acid, under conditions wherein a donor-target integration reaction product is formed and wherein said first domain of said chimeric protein directly or indirectly binds to said regulatory region, and
   locating the gene by detecting the site of integration of said donor nucleic acid, wherein said site of integration is located in said regulatory region of said gene.

15. A method according to claim 14, wherein said chimeric protein directly binds to the regulatory region.

16. A method according to claim 14, wherein said donor nucleic acid comprises at least one end region of a retroviral long terminal repeat.

17. A method according to claim 16, wherein said donor nucleic acid is a retroviral vector.

18. A method according to claim 14, wherein said donor nucleic acid has a detectable label.

* * * * *